(12) United States Patent
Tanaka et al.

(10) Patent No.: US 7,279,574 B2
(45) Date of Patent: Oct. 9, 2007

(54) EPOXY COMPOUND AND CURED EPOXY RESIN PRODUCT

(75) Inventors: Shinya Tanaka, Osaka (JP); Yoshitaka Takezawa, Hitachi (JP); Hiroyuki Takahashi, Hitachi (JP)

(73) Assignees: Sumitomo Chemical Company, Limited, Tokyo (JP); Hitachi, Ltd., Tokyo (JP)

( * ) Notice: Subject to any disclaimer, the term of this patent is extended or adjusted under 35 U.S.C. 154(b) by 0 days.

(21) Appl. No.: 10/560,891

(22) PCT Filed: Jun. 18, 2004

(86) PCT No.: PCT/JP2004/008934

§ 371 (c)(1),
(2), (4) Date: Jan. 20, 2006

(87) PCT Pub. No.: WO2004/113327

PCT Pub. Date: Dec. 29, 2004

(65) Prior Publication Data

US 2006/0159929 A1    Jul. 20, 2006

(30) Foreign Application Priority Data

Jun. 19, 2003    (JP)    ............... 2003-174545

(51) Int. Cl.
*C07D 401/00*    (2006.01)
*C07D 237/00*    (2006.01)
*C07D 405/00*    (2006.01)
*C07D 211/00*    (2006.01)
*C07D 303/12*    (2006.01)
*C08G 59/14*    (2006.01)
*C08F 283/00*    (2006.01)
*C08L 63/00*    (2006.01)

(52) U.S. Cl. ................ 544/238; 544/239; 546/281.7; 546/296; 549/560; 525/507; 525/122; 525/523; 525/533

(58) Field of Classification Search .......... 546/281.7, 546/296; 544/238, 239, 309; 549/560; 528/406, 528/407, 423; 525/507, 122, 523, 533
See application file for complete search history.

(56) References Cited

U.S. PATENT DOCUMENTS 5,569,727 A    10/1996    Mormann et al.
5,851,427 A    12/1998    Kelly
5,904,984 A    5/1999    Smith et al.

FOREIGN PATENT DOCUMENTS

GB    2 338 240    12/1999
JP    63006015 A  *    1/1988

OTHER PUBLICATIONS

Broer, D. J.; Lub, J., and Mol, G. N. "Synthesis and Photopolymerization of a Liquid-Crystalline Diepoxide" Macromolecules 1993, 26, 1244-1247.*
Mallon, Joseph J.; Adams, Paul M. "Synthesis and characterization of novel epoxy monomers and liquid crystal thermosets." Journal of Polymer Science, Part A: Polymer Chemistry 1993, 31(9), 2249-60.*
Kostromin, S. G.; Tuan, Pham Anh; Shibaev, V.P. "Liquid crystal poly(a-oxiranes) with mesogenic side group." Vysokomolekulyarnye Soedineniya, Seriya A i Seriya B 1994, 36(11), 1807-16 (abstract only).*
N. Baraskov et al., "Design of New Polymers to Improve Radiation Stability of Plastic Scintillators", Proceedings of the Fourth International Conference on Calorimetry in High Energy Physics, pp. 542-551, XP009037802, 1993.

* cited by examiner

*Primary Examiner*—Rita Desai
*Assistant Examiner*—David K O'Dell
(74) *Attorney, Agent, or Firm*—Wenderoth, Lind & Ponack, L.L.P.

(57) ABSTRACT

The present invention provides a novel epoxy compound, which can be converted into a cured epoxy resin product having liquid crystal properties by curing with a curing agent. Since the cured epoxy resin product of the present invention exhibits good heat conductivity, it is also useful as an insulating material requiring high heat releasability such as a printed circuit substrate and the like.

11 Claims, No Drawings

EPOXY COMPOUND AND CURED EPOXY RESIN PRODUCT

TECHNICAL FIELD

The present invention relates to an epoxy compound and a cured epoxy resin product.

BACKGROUND ART

For example, cured epoxy resin products obtained by curing epoxy compounds such as 4-(oxiranylmethoxy)benzoic acid-1,8-octanediyl bis(oxy-4,1-phenylene)ester and 4,4'-biphenol glycidyl ether and diamine compounds such as diaminodiphenylmethane are known to have liquid crystal properties (for example, JP-A No. 9-118673, and JP-A No. 11-323162).

DISCLOSURE OF INVENTION

In order to provide a novel epoxy compound which can be converted into a novel cured epoxy resin product having liquid crystal properties, the present inventors intensively studied and found that an epoxy compound having a specific divalent group such as a pyridin-2,6-diyl group and a specific group such as a biphenylene group can be converted into such a cured epoxy resin product having liquid crystal properties, which resulted in completion of the present invention.

That is, the present invention provides an epoxy compound of the formula (1):

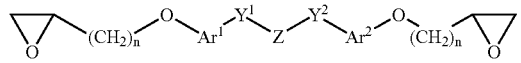
(1)

wherein n represents an integer of 1 to 9, the $—(CH_2)_n—$ group may have inserted —O—, or —N(R')—, between the methylene groups, wherein R' represents a hydrogen atom or a $C_{1-18}$ alkyl group, Z represents any one of divalent groups of the following formulas (Z-1) to (Z-7):

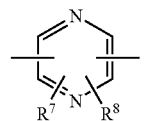
(Z-1)

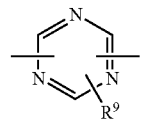
(Z-2)

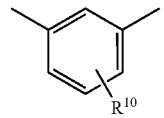
(Z-3)

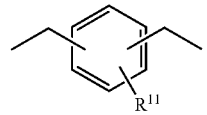
(Z-4)

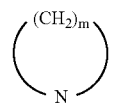
(Z-5)

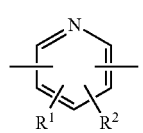
(Z-6)

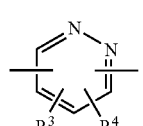
(Z-7)

wherein $R^1$, $R^2$, $R^3$, $R^4$, $R^5$, $R^6$, $R^7$, $R^8$, $R^9$, $R^{10}$ and $R^{11}$ are the same or different and represent independently a hydrogen atom, a $C_{1-18}$ alkyl group, an amino group substituted with one or two $C_{1-18}$ alkyl groups, or a cyclic amino group of the following formula:

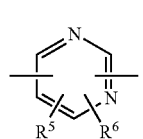

wherein m represents an integer of 4 to 12, and one methylene group or two or more not neighboring methylene groups of the $C_{1-18}$ alkyl group or groups as defined in connection with $R^1$, $R^2$, $R^3$, $R^4$, $R^5$, $R^6$, $R^7$, $R^8$, $R^9$, $R^{10}$ or $R^{11}$, and of the cyclic amino group, may be replaced with —O—, —NH—, —N(R")— or —S—, wherein R" represents a $C_{1-18}$ alkyl group, $Ar^1$ and $Ar^2$ are the same or different and represent any one of groups of the following formulas (A-1) to (A-3):

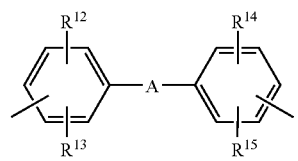
(A-1)

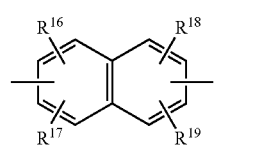
(A-2)

-continued

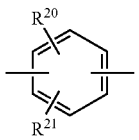
(A-3)

wherein A represents a single bond or any one group selected from the group consisting of:

—CH═CH—  —C≡C—  —CH═N—

—N═N—  —C═CH—
              |
              R²²

—CH═CH—C—  —O—C—
         ‖       ‖
         O       O wherein $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are the same or different and represent independently a hydrogen atom, a halogen atom, a $C_{1-8}$ alkyl group, a $C_{1-8}$ alkoxy group, a cyano group, or a nitro group, $Y^1$ and $Y^2$ are the same or different and represent a single bond, —O—, —S—, or —Si($R^{23}$)($R^{24}$)—, wherein $R^{23}$ and $R^{24}$ are the same or different and represent independently a lower alkyl group or a phenyl group;

an epoxy composition containing the epoxy compound and a curing agent; and a cured epoxy resin product obtained by curing the epoxy composition.

The epoxy compound of the present invention is a novel compound, which can be converted-into a cured epoxy resin product having liquid crystal properties by curing with a curing agent. Since the cured epoxy resin product of the present invention exhibits good heat conductivity, it is also useful as an insulating material requiring high heat releasability such as a printed circuit substrate and the like.

BEST MODE FOR CARRYING OUT THE INVENTION

In the epoxy compound of following formula (1):

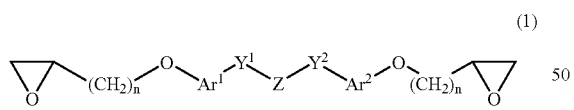
(1)

(hereinafter, abbreviated as epoxy compound (1)) of the present invention, n represents an integer of 1 to 9, preferably an integer of 1 to 4, particularly preferably 1, the —(CH₂)— group(s) may have inserted —O—, or —N(R')—, between the methylene groups, wherein R' represents a hydrogen atom or a $C_{1-18}$ alkyl group, (e.g. straight or branched $C_{1-18}$ alkyl groups such as methyl, ethyl, n-propyl, isopropyl, n-butyl, isobutyl, sec-butyl, tert-butyl, n-pentyl, n-hexyl, n-heptyl, n-octyl, 1,1,3,3-tetramethylbutyl, n-nonyl, n-decyl, n-undecyl, n-dodecyl, n-tridecyl, n-tetradecyl, n-pentadecyl, n-hexadecyl, n-heptadecyl, or n-octadecyl), Z represents any one of divalent groups of the following formulas (Z-1) to (Z-7):

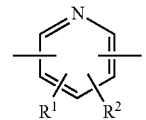
(Z-1)

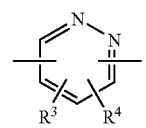
(Z-2)

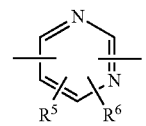
(Z-3)

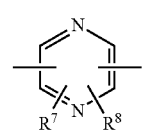
(Z-4)

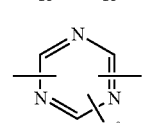
(Z-5)

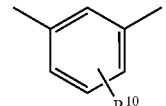
(Z-6)

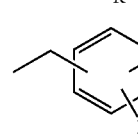
(Z-7)

wherein $R^1$, $R^2$, $R^3$, $R^4$, $R^5$, $R^6$, $R^7$, $R^8$, $R^9$, $R^{10}$ and $R^{11}$ are the same or different and represent independently a hydrogen atom, a $C_{1-18}$ alkyl group, an amino group substituted with one or two $C_{1-18}$ alkyl groups, or a cyclic amino group of the following formula:

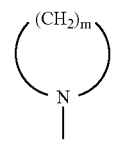

wherein m represents an integer of 4 to 12, and one methylene group or two or more not neighboring methylene groups of the $C_{1-18}$ alkyl group or groups as defined in connection with $R^1$, $R^2$, $R^3$, $R^4$, $R^5$, $R^6$, $R^7$, $R^8$, $R^9$, $R^{10}$ or $R^{11}$, and of the cyclic amino group, may be replaced with —O—, —NH—, —N(R")— or —S—, wherein R" represents a $C_{1-18}$ alkyl group, Inter alia, the divalent group wherein $R^1$, $R^2$, $R^3$, $R^4$, $R^5$, $R^6$, $R^7$, $R^8$, $R^9$, $R^{10}$ and $R^{11}$ represent a hydrogen atom, is preferable.

Examples of the —(CH₂)ₙ— group that has inserted —O—, or —N(R')— between the methylene groups, wherein R' represents a hydrogen atom or a $C_{1-18}$ alkyl group, include 2-oxa-1,4-butandiyl, 2-imino-1,4-butandiyl, 2,5-dioxa-1,7-heptandiyl, and 2,5,8-trioxa-1,10-decandiyl group.

One methylene group or two or more not neighboring methylene groups of the $C_{1-18}$ alkyl group or groups as defined in connection with $R^1$, $R^2$, $R^3$, $R^4$, $R^5$, $R^6$, $R^7$, $R^8$, $R^9$, $R^{10}$ or $R^{11}$, which $C_{1-18}$ alkyl group means the $C_{1-18}$ alkyl group represented by $R^1$, $R^2$, $R^3$, $R^4$, $R^5$, $R^6$, $R^7$, $R^8$, $R^9$, $R^{10}$ or $R^{11}$ and the $C_{1-18}$ alkyl group or groups of the amino group substituted with one or two $C_{1-18}$ alkyl groups, may be replaced with —O—, —NH—, —N(R")— or —S— wherein R" represents a $C_{1-18}$ alkyl group, and examples of the alkyl group of which methylene group is replaced with —O—, —NH—, —N(R")— or —S— include methoxy, ethoxy, n-propoxy, isopropoxy, n-butoxy, isobutoxy, sec-butoxy, tert-butoxy, n-pentyloxy, n-hexyloxy, n-octyloxy, 1,1,3,3-tetramethylbutyloxy, n-decyloxy, n-dodecyloxy, n-pentadecyloxy, n-octadecyloxy, 2-methoxyethyl, 2-methoxyethoxy, methylthio, and 2-(dimethylamino)ethyl.

Examples of the $C_{1-18}$ alkyl group represented by $R^1$, $R^2$, $R^3$, $R^4$, $R^5$, $R^6$, $R^7$, $R^8$, $R^9$, $R^{10}$ or $R^{11}$ or contained therein, or represented by R" include the straight or branched $C_{1-18}$ alkyl groups exemplified above for R'.

Examples of the amino groups substituted with one or two $C_{1-18}$ alkyl groups include amino groups substituted with the aforementioned one $C_{1-18}$ alkyl group such as methylamino, ethylamino, isopropylamino, or n-hexylamino, amino groups substituted with the aforementioned two $C_{1-18}$ alkyl groups such as dimethylamino, diethylamino, or methylethylamino.

Examples of the cyclic amino group of the following formula:

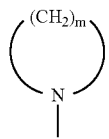

include 1-pyrrolidino, 1-piperidino, and 4-morpholino. One methylene group or two or more not neighboring methylene groups, constituting such amino and cyclic amino groups, may be replaced with —O—, —NH—, —N(R")— or —S—, wherein R" represents a $C_{1-18}$ alkyl group, and examples of the amino and cyclic amino groups of which methylene group is replaced with —O— or the like include, for example, 2-methoxyethylamino and 4-morpholino.

Examples of the divalent group of formulas (Z-1) to (Z-7) include 2,4-pyridinediyl, 2,5-pyridinediyl, 3,5-pyridinediyl, 2,3-pyridinediyl, 2,6-pyridinediyl, 4-methyl-2,6-pyridinediyl, 2-methyl-4,6-pyridinediyl, 3,6-pyridazinediyl, 4,5-pyridazinediyl, 4-methyl-3,6-pyridazinediyl, 2,4-pyrimidinediyl, 4,6-pyrimidinediyl, 6-methyl-2,4-pyrimidinediyl, 5-methyl-2,4-pyrimidinediyl, 2,3-pyrazinediyl, 2,6-pyrazinediyl, 2,6-triazinediyl, 4-(4-morpholino)-2,6-triazinediyl, 4-[(1,1,3,3-tetramethylbutyl)amino]-2,6-triazinediyl, 1,3-phenylene, benzene-1,3-dimethylene, and benzene-1,4-dimethylene. Among these divalent groups of formulas (Z-1) to (Z-7), for example, divalent groups of the formula (Z-1) such as 2,4-pyridinediyl, 2,5-pyridinediyl, 3,5-pyridinediyl, 2,3-pyridinediyl, 2,6-pyridinediyl, 4-methyl-2,6-pyridinediyl, and 2-methyl-4,6-pyridinediyl are preferable, and 2,4-pyridinediyl, 2,5-pyridinediyl, 3,5-pyridinediyl, 2,3-pyridinediyl and 2,6-pyridinediyl are more preferable, and 2,6-pyridinediyl is still more preferable.

$Ar^1$ and $Ar^2$ in the afore-mentioned formula (1) are the same or different and represent independently any one of groups of the following formulas (A-1) to (A-3):

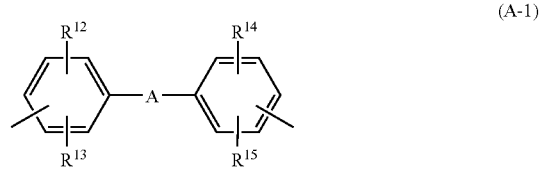

(A-1)

(A-2)

(A-3)

wherein A represents a single bond or any one group selected from the group consisting of:

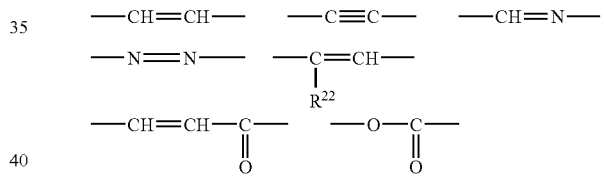

wherein $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are the same or different and represent independently a hydrogen atom, a halogen atom, a $C_{1-8}$ alkyl group, a $C_{1-8}$ alkoxy group, a cyano group, or a nitro group. $Ar^1$ and $Ar^2$ are preferably the same.

Examples of the halogen atom include a fluorine atom, a chlorine atom, a bromine atom, and an iodine atom and examples of the $C_{1-8}$ alkyl group include straight or branched $C_{1-8}$ alkyl groups such as methyl, ethyl, n-propyl, isopropyl, n-butyl, isobutyl, sec-butyl, tert-butyl, n-pentyl, n-hexyl, n-octyl, and 1,1,3,3-tetramethylbutyl. Examples of the $C_{1-8}$ alkoxy include straight or branched $C_{1-8}$ alkoxy groups such as methoxy, ethoxy, n-propoxy, isopropoxy, n-butoxy, isobutoxy, sec-butoxy, tert-butoxy, n-pentyloxy, n-hexyloxy, n-octyloxy, and 1,1,3,3-tetramethylbutyloxy.

Examples of the groups of the formulas (A-1) to (A-3) include 4,4'-biphenylene, 3,3',5,5'-tetramethyl-4,4'-5 biphenylene, 1,5-naphthylene, 1,6-naphthylene, 1,7-naphthylene, 2,6-naphthylene, 2,7-naphthylene, 1,3-phenylene and 1,4-phenylene. Among the groups of the formulas (A-1) to (A-3), groups of the formula (A-1) are preferable, and groups of the following formula:

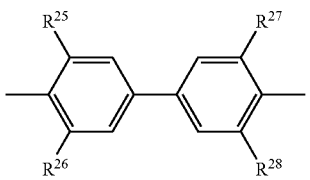

wherein $R^{25}$, $R^{26}$, $R^{27}$ and $R^{28}$ are the same or different and represent independently a hydrogen atom or a methyl group, are more preferable.

$Y^1$ and $Y^2$ are the same or different and represent independently a single bond, —O—, —S—, or —Si($R^{23}$)($R^{24}$)—, and $R^{23}$ and $R^{24}$ are the same or different and represent independently a lower alkyl group or a phenyl group. Examples of the lower alkyl group include $C_{1-4}$ alkyl groups such as methyl, ethyl, n-propyl, isopropyl, n-butyl, isobutyl, sec-butyl or tert-butyl, and examples of the group of —Si($R^{23}$)($R^{24}$)— include, for example, dimethylsilylene. Inter alia, as $Y^1$ and $Y^2$, —O— is preferable.

Examples of such an epoxy compound (1) include 2,6-bis[4-(oxiranylmethoxy)phenoxy]pyridine, 2,6-bis[4-[4-(oxiranylmethoxy)phenyl]phenoxy]pyridine, 2,6-bis[4-[4-(oxiranylbutoxy)phenyl]phenoxy]pyridine, 2,6-bis[6-(oxiranylmethoxy)-2-naphthoxy]pyridine, 2,6-bis[4-(oxiranylmethoxy)phenoxy]-4-methylpyridine, 2,6-bis[4-[4-(oxiranylmethoxy)phenyl]phenoxy-4-methylpyridine, 2,6-bis[4-[4-(4-oxiranylbutoxy)phenyl]phenoxy]-4-methylpyridine, 2,6-bis[6-(oxiranylmethoxy)-2-naphthoxy]-4-methylpyridine, 2,5-bis[4-(oxiranylmethoxy)phenoxy]pyridine, 2,5-bis[4-[4-(oxiranylmethoxy)phenyl]phenoxy]pyridine, 2,5-bis[4-[4-(4-oxiranylbutoxy)phenyl]phenoxy]pyridine, 2,5-bis[6-(oxiranylmethoxy)-2-naphthoxy]pyridine, 2,4-bis[4-(oxiranylmethoxy)phenoxy]pyridine, 2,4-bis[4-[4-(oxiranylmethoxy)phenyl]phenoxy]pyridine, 2,4-bis[4-[4-oxiranylbutoxy)phenyl]phenoxy]pyridine, 2,4-bis[6-(oxiranylmethoxy)-2-naphthoxy]pyridine, 3,5-bis(4-(oxiranylmethoxy)phenoxy]pyridine, 3,5-bis[4-[4-(oxiranylmethoxy)phenyl]phenoxy]pyridine, 3,5-bis[4-[4-(4-oxiranylbutoxy)phenyl]phenoxypyridine, 3,5-bis[6-(oxiranylmethoxy)-2-naphthoxy]pyridine, 4,6-bis[4-(oxiranylmethoxy)phenoxy]-2-methylpyridine, 4,6-bis[4-[4-(oxiranylmethoxy)phenyl]phenoxy]-2-methylpyridine, 4,6-bis[4-[4-(4-oxiranylbutoxy)phenyl]-2-methylphenoxy]pyridine, 4,6-bis[6-(oxiranylmethoxy)-2-naphthoxy]-2-methylpyridine, 3,6-bis[4-(oxiranylmethoxy)phenoxy]pyridazine, 3,6-bis[4-[4-(oxiranylmethoxy)phenyl]phenoxy]pyridazine, 3,6-bis[4-[4-(4-oxiranylbutoxy)phenyl]phenoxy]pyridazine, 3,6-bis[6-(oxiranylmethoxy)-2-naphthoxy]pyridazine, 3,6-bis[4-(oxiranylmethoxy)phenoxy]-4-methylpyridazine, 3,6-bis[4-[4-(oxiranylmethoxy)phenyl]phenoxy]-4-methylpyridazine, 3,6-bis[4-[4-(4-oxiranylbutoxy)phenyl]phenoxy]-4-methylpyridazine, 3,6-bis[6-(oxiranylmethoxy)-2-naphthoxy]-4-methylpyridazine, 2,4-bis[4-(oxiranylmethoxy)phenoxy]pyrimidine, 2,4-bis[4-[4-(oxiranylmethoxy)phenyl]phenoxy]pyrimidine, 2,4-bis[4-[4-(4-oxiranylbutoxy)phenyl]phenoxy]pyrimidine, 2,4-bis[6-(oxiranylmethoxy)-2-naphthoxy]pyrimidine, 4,6-bis[4-(oxiranylmethoxy)phenoxy]pyrimidine, 4,6-bis[4-(oxiranylmethoxy)phenyl]phenoxy]pyrimidine, 4,6-bis[4-[4-(4-oxiranylbutoxy)phenyl]phenoxy]pyrimidine, 4,6-bis[6-(oxiranylmethoxy)-2-naphthoxy]pyrimidine, 2,4-bis[4-(oxiranylmethoxy)phenoxy]-6-methylpyrimidine, 2,4-bis[4-[4-(oxiranylmethoxy)phenyl]phenoxy]-6-methylpyrimidine, 2,4-bis[4-(4-(4-oxiranylbutoxy)phenyl]phenoxy]-6-methylpyrimidine, 2,4-bis[6-(oxiranylmethoxy)-2-naphthoxy]-6-methylpyrimidine, 2,4-bis[4-(oxiranylmethoxy)phenoxy]-5-methylpyrimidine, 2,4-bis[4-[4-(oxiranylmethoxy)phenyl]phenoxy]-5-methylpyrimidine, 2,4-bis[4-[4-(4-oxiranylbutoxy)phenyl]phenoxy]-5-methylpyrimidine, 2,4-bis[6-(oxiranylmethoxy)-2-naphthoxy]-5-methylpyrimidine, 2,6-bis[4-(oxiranylmethoxy)phenoxy]pyrazine, 2,6-bis[4-[4-(oxiranylmethoxy)phenyl]phenoxy]pyrazine, 2,6-bis[4-[4-(4-oxiranylbutoxy)phenyl]phenoxy]pyrazine, 2,6-bis[6-(oxiranylmethoxy)-2-naphthoxy]pyrazine, 2,6-bis[4-(oxiranylmethoxy)phenoxy]triazine, 2,6-bis[4-[4-(oxiranylmethoxy)phenyl]phenoxy]triazine, 2,6-bis[4-[4-(4-oxiranylbutoxy)phenyl]phenoxy]triazine, 2,6-bis[6-(oxiranylmethoxy)-2-naphthoxy]triazine, 2,6-bis[4-(oxiranylmethoxy)phenoxy]-4-(4-morpholino)triazine, 2,6-bis[4-[4-(oxiranylmethoxy)phenyl]phenoxy]-4-(4-morpholino)triazine, 2,6-bis[4-[4-(4-oxiranylbutoxy)phenyl]phenoxy]-4-(4-morpholino)triazine, 2,6-bis[6-(oxiranylmethoxy)-2-naphthoxy)-4-(4-morpholino)triazine, 2,6-bis[4-(oxiranylmethoxy)phenoxy]-4-[(1,1,3,3-tetramethylbutyl)amino]triazine, 2,6-bis[4-[4-(oxiranylmethoxy)phenyl]phenoxy]-4-[(1,1,3,3-tetramethylbutyl)amino]triazine, 2,6-bis[4-[4-(4-oxiranylbutoxy)phenyl]phenoxy]-4-[(1,1,3,3-tetramethylbutyl)amino]triazine, 2,6-bis[6-(oxiranylmethoxy)-2-naphthoxy]-4-[(1,1,3,3-tetramethylbutyl)amino]triazine, 1,3-bis[4-(oxiranylmethoxy)phenoxy]benzene, 1,3-bis[4-[4-(oxiranyliaethoxy)phenyl]phenoxy]benzene, 1,3-bis[4-[4-(4-oxiranylbutoxy)phenyl]phenoxy]benzene, 1,3-bis[6-(oxiranylmethoxy)-2-naphthoxy]benzene, 1,3-bis[[4-(oxiranylmethoxy)phenoxy]methyl]benzene, 1,3-bis[[4-[4-(oxiranylmethoxy)phenyl]phenoxy]methyl]benzene, 1,3-bis[[4-[4-(4-oxiranylbutoxy)phenyl]phenoxy]methyl]benzene, 1,3-bis[[6-(oxiranylmethoxy)-2-naphthoxy]methyl]benzene, 1,4-bis[[4-(oxiranylmethoxy)phenoxy]methyl]benzene, 1,4-bis[[4-[4-(oxiranylmethoxy)phenyl]phenoxy]methyl]benzene, 1,4-bis[[4-[4-(4-oxiranylbutoxy)phenyl]phenoxy]methyl]benzene, 1,4-bis[[6-(oxiranylmethoxy)-2-naphthoxy]methyl]benzene, 2-[4-(oxiranylmethoxy)phenoxy]-6-[4-[4-(oxiranylmethoxy)phenyl]phenoxy]pyridine, 2-[4-(oxiranylmethoxy)phenoxy]-6-[6-(oxiranylmethoxy)-2-naphthoxy]pyridine, 2-[4-[4-(oxiranylmethoxy)phenyl]phenoxy]-6-[6-(oxiranylmethoxy)-2-naphthoxy]pyridine, 2,6-bis[4-[2-(oxiranylmethoxy)ethoxy]phenyl]phenoxy]pyridine, 2,6-bis[4-[4-[2-(oxiranylmethoxy)aminoethoxy]phenyl]phenoxy]pyridine, 2,6-bis[4-[4-[7-(oxiranyl-3,6-dioxaheptyloxy)-phenyl]phenoxy]pyridine, and 2,6-bis[4-[4-(10-(oxiranyl-3,6,9-trioxadecyloxy)phenyl]phenoxy]pyridine.

Such an epoxy compound (1) can be prepared, for example, by a process of reacting an alcohol compound of the following formula (2) (hereinafter, abbreviated as alcohol compound (2)):

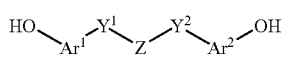

(2)

wherein Z, $Ar^1$, $Ar^2$, $Y^1$ and $Y^2$ are as defined above, with a compound of the following formula (3) (hereinafter, abbreviated as a compound (3)):

(3)

wherein X represents a chlorine atom, a bromine atom, or an iodine atom, and n is as defined above, in the presence of a base, or by a process of reacting the alcohol compound (2) and a compound (4) of the following formula (4) (hereinafter, abbreviated as a compound (4)):

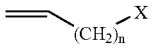

(4)

wherein X and n are as defined above, in the presence of a base, followed by oxidation (epoxydation).

Examples of the alcohol compound (2) include 2,6-bis(4-hydroxyphenoxy)pyridine, 2,6-bis[4-(4-hydroxyphenyl)phenoxy]pyridine, 2,6-bis(6-hydroxy-2-naphthoxy)pyridine, 2,6-bis(4-hydroxyphenoxy)-4-methylpyridine, 2,6-bis[4-(4-hydroxyphenyl)phenoxy]-4-methylpyridine, 2,6-bis(6-hydroxy-2-naphthoxy)-4-methylpyridine, 2,5-bis(4-hydroxyphenoxy)pyridine, 2,5-bis(4-(4-hydroxyphenyl)phenoxy]pyridine, 2,5-bis(6-hydroxy-2-naphthoxy)pyridine, 2,4-bis(4-hydroxyphenoxy)pyridine, 2,4-bis[4-(4-hydroxyphenyl)phenoxy]pyridine, 2,4-bis(6-hydroxy-2-naphthoxy)pyridine, 3,5-bis(4-hydroxyphenoxy) pyridine, 3,5-bis[4-(4-hydroxyphenyl)phenoxy]pyridine, 3,5-bis(6-hydroxy-2-naphthoxy)pyridine, 4,6-bis(4-hydroxyphenoxy)-2-methylpyridine, 4,6-bis[4-(4-hydroxyphenyl)phenoxy]-2-methylpyridine, 4,6-bis(6-hydroxy-2-naphthoxy)-2-methylpyridine, 3,6-bis(4-hydroxyphenoxy)pyridazine, 3,6-bis[4-(4-hydroxyphenyl)phenoxy]pyridazine, 3,6-bis(6-hydroxy-2-naphthoxy)pyridazine, 3,6-bis(4-hydroxyphenoxy)-4-methylpyridazine, 3,6-bis[4-(4-hydroxyphenyl)phenoxy]-4-methylpyridazine, 3,6-bis(6-hydroxy-2-naphthoxy)-4-methylpyridazine, 2,4-bis(4-hydroxyphenoxy)pyrimidine, 2,4-bis[4-(4-hydroxyphenyl)phenoxy]pyrimidine, 2,4-bis(6-hydroxy-2-naphthoxy)pyrimidine, 4,6-bis(4-hydroxyphenoxy)pyrimidine, 4,6-bis[4-(4-hydroxyphenyl)phenoxy]pyrimidine, 4,6-bis(6-hydroxy-2-naphthoxy)pyrimidine, 2,4-bis(4-hydroxyphenoxy)-6-methylpyrimidine, 2,4-bis[4-(4-hydroxyphenyl)phenoxy]-6-methylpyrimidine, 2,4-bis(6-hydroxy-2-naphthoxy)-6-methylpyrimidine, 2,4-bis(4-hydroxyphenoxy)-5-methylpyrimidine, 2,4-bis[4-(4-hydroxyphenyl)phenoxy]-5-methylpyrimidine, 2,4-bis(6-hydroxy-2-naphthoxy)-5-methylpyrimidine, 2,6-bis(4-hydroxyphenoxy)pyrazine, 2,6-bis[4-(4-hydroxyphenyl)phenoxy]pyrazine, 2,6-bis(6-hydroxy-2-naphthoxy)pyrazine, 2,6-bis(4-hydroxyphenoxy)triazine, 2,6-bis[4-(4-hydroxyphenyl)phenoxy]triazine, 2,6-bis(6-hydroxy-2-naphthoxy)triazine, 2,6-bis(4-hydroxyphenoxy)-4-(4-morpholino)triazine, 2,6-bis[4-(4-hydroxyphenyl)phenoxy]-4-(4-morpholino)triazine, 2,6-bis(6-hydroxy-2-naphthoxy)-4-(4-morpholino)triazine, 2,6-bis(4-hydroxyphenoxy)-4-[(1,1,3,3-tetramethylbutyl)amino]triazine, 2,6-bis[4-(4-hydroxyphenyl)phenoxy]-4-[(1,1,3,3-tetramethylbutyl)amino]triazine, 2,6-bis(6-hydroxy-2-naphthoxy)-4-[(1,1,3,3-tetramethylbutyl)amino]triazine, 1,3-bis(4-hydroxyphenoxy)benzene, 1,3-bis[4-(4-hydroxyphenyl)phenoxy]benzene, 1,3-bis(6-hydroxy-2-naphthoxy)benzene, 1,3-bis[(4-hydroxyphenoxy)methyl]benzene, 1,3-bis[[4-(4-hydroxyphenyl)phenoxy]methyl]benzene, 1,3-bis[(6-hydroxy-2-naphthoxy)methyl]benzene, 1,4-bis[(4-hydroxyphenoxy)methyl]benzene, 1,4-bis[[4-(4-hydroxyphenyl)phenoxy]methyl]benzene, 1,4-bis[(6-hydroxy-2-naphthoxy)methyl]benzene, 2-(4-hydroxyphenoxy)-6-[4-(4-hydroxyphenyl)phenoxy]pyridine, 2-(4-hydroxyphenoxy)-6-(6-hydroxy-2-naphthoxy)pyridine, and 2-[4-(4-hydroxyphenyl)phenoxy]-6-(6-hydroxy-2-naphthoxy)pyridine.

First, the process of preparing the epoxy compound (1) by reacting the alcohol compound (2) and the compound (3) in the presence of a base will be explained.

Examples of the compound (3) include epichlorohydrin, epibromohydrin, 2-oxiranyl-1-chloroethane and 4-oxiranyl-1-chlorobutane. Epichlorohydrin and epibromohydrin are preferable. The amount of compound (3) that may be used is generally 2 to 100 moles, preferably 5 to 30 moles per mol of the alcohol compound (2).

Examples of the base include an inorganic base such as sodium hydroxide and potassium hydroxide, and an amount of the base that may be used is generally 2 to 5 moles per mol of the alcohol compound (2).

The reaction of the alcohol compound (2) with the compound (3) is carried out generally by mixing both compounds in & solvent in the presence of a base, and said mixing may be conducted in an optional order. The solvent that may be used is not particularly limited as far as it is inert to the reaction, but from a viewpoint of easy suppression of byproduct formation, a hydrophilic solvent is preferable. Examples of the hydrophilic solvent include alcohol type solvents such as methanol, ethanol, propanol, butanol, ethylene glycol., and propylene glycol, ketone type solvents such as methyl ethyl ketone or methyl isobutyl ketone, non-protonic polar solvents such as N,N-dimethylformamide, dimethyl sulfoxide, or N-methylpyrrolidone, ether type solvents such as tetrahydrofuran, dioxane, methoxymethyl ether, or diethoxyetbane, and mixtures thereof. Inter alia, ether type solvents, aprotic polar solvents, and a mixture thereof are preferable. Aprotic polar solvents are more preferable and, inter alia, dimethyl sulfoxide is particularly preferable. An amount of the solvent that may be used is generally 0.1 to 50 parts by weight, preferably 0.5 to 5 parts by weight per part by weight of the alcohol compound (2).

The reaction may be carried out under normal pressure or under reduced pressure. A reaction temperature is generally 10 to 150° C. And, this reaction produces water as a byproduct along with progress of the reaction depending on a type of the base to be used. In such a case, it is preferable to carry out the reaction while water as the byproduct is removed from the reaction system, and it is preferable to carry out the reaction at a reaction temperature or a reaction pressure at which water is removed by azeotroping.

After completion of the reaction, for example, the remaining compound (3) is removed and, if necessary, a hydrophilic solvent is added, and insoluble matters are removed by filtration and then the resulting reaction solution is concentrated or cooled to obtain the epoxy compound (1). The obtained epoxy compound (1) may be further purified by a conventional purification means, for example, by recrystallization.

Next, the process of reacting the alcohol compound (2) with the compound (4) in the presence of a base, followed by oxidation, will be explained.

Examples of the compound (4) include allyl chloride, allyl bromide, and 1-chloro-5-hexene. An amount of the compound (4) that may be used is generally 2 to 100 moles, preferably 3 to 30 moles per mol of the alcohol compound (2).

Examples of the base include inorganic bases such as sodium hydroxide or potassium hydroxide, and organic bases such as pyridine. An amount of the base that may be used is generally 2 to 5 moles per mol of the alcohol compound (2). In the case of using an organic base, which is liquid under the reaction condition, an excess amount of such an organic base may be used also as a reaction solvent.

The reaction of the alcohol compound (2.) with the compound (4) is carried out generally by mixing both compounds in a solvent in the presence of the base, and an order of mixing is not particularly limited. Examples of the solvent include the same solvents as those exemplified for the case of the reaction of the alcohol compound (2) with the compound (3). Also, as described above, in the case of using an organic base, which is liquid under the reaction conditions, the organic base may be used as the reaction solvent.

The reaction may be carried out under normal pressure or under reduced pressure. A reaction temperature is generally 10 to 150° C. And, this reaction produces water as a byproduct along with progress of the reaction depending on a type of the base used. In such a case, it is preferable to carry out the reaction while water as the byproduct is removed from the reaction system, and it is preferable to carry out the reaction at a reaction temperature or a reaction pressure at which water is removed by azeotroping.

After completion of the reaction, an oxidizing agent may be added to the reaction system as it is to epoxidize the product from the reaction of the alcohol compound (2) with the compound (4). Alternatively, after the reaction solution is mixed with water to separate the product from the reaction of the alcohol compound (2) with the compound (4), an oxidizing agent may be added to epoxidize the reaction product. As the oxidizing agent, any suitable oxidizing agent may be used as far as it can epoxidize carbon-carbon double bonds and, for example, m-chloroperbenzoic acid can be exemplified. An amount of the oxidizing agent that may be used is generally 2 to 10 moles per mol of the reaction product of the alcohol compound (2) and the compound (4).

After epoxidation by the oxidizing agent the remaining oxidizing agent is decomposed if necessary, followed by concentration, to separate the epoxy compound (1). The separated epoxy compound (1) may be further purified by a conventional purification means, for example, by recrystallization.

An epoxy compound of formula (1), wherein the —(CH$_2$)$_n$— group has, between the methylene groups, inserted —O—, or —N(R')— such as 2,6-bis[4-[4-[2-(oxiranylmethoxy)-ethoxy]phenyl]phenoxy]pyridine can be produced, for example, by a process which comprises reacting a compound of formula (12):

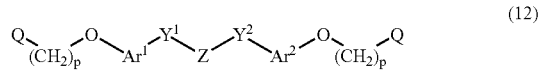

(12)

wherein Ar$^1$, Ar$^2$, Y$^1$, Y$^2$ and Z are as defined above, Q represents a hydroxyl group or —NH(R')—, p is an integer of 1 to 8, wherein the —(CH$_2$)$_p$— may have, between the methylene groups, inserted —O—, or —N(R')—, wherein R' is as defined above (hereinafter abbreviated as compound (12)), with a compound of formula (13):

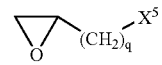

(13)

wherein X$^5$ represents a chlorine, bromine or iodine atom, q is an integer of 1 to 8, provided that p+q=2 to 9(hereinafter abbreviated as compound (13)), in the presence of a base (e.g. inorganic base as described above, a tertiary amine such as triethylamine or pyridine, and preferably mixtures of the inorganic base and the tertiary amine (see JP-A-7-179447)).

Examples of the compound (12) include, for example, 2,6-bis[4-(4-(2-hydroxyethoxy)phenyl]phenoxy]pyridine, 2,6-bis[4-[4-(2-aminoethoxy)phenyl]phenoxy]pyridine, 2,6-bis[4-[4-(5-hydroxy-3-oxapentyloxy)phenyl]phenoxy]pyridine, 2,6-bis[4-[4-(8-hydroxy-3,6-dioxaoctyloxy)phenyl]phenoxy]-pyridine and the like.

As the examples of the compound (13), the compound (3) as exemplified above is referred to. The reaction of the compound (12) with the compound (13) is usually carried out in a similar manner as the reaction of the alcohol compound (2) described above with the compound. (3).

Next, a process of preparing the alcohol compound (2) will be described. Among alcohol compounds (2), compounds (2), wherein Z is a divalent group of (Z-1) to (Z-5) or (Z-7), and Y$^1$ and Y$^2$ are the same or different and represent independently —O—, —S—, or —Si(R$^{23}$)(R$^{24}$)— can be prepared, for example, by reacting a compound of the following formula (5) (hereinafter, abbreviated as compound (5)):

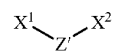

(5)

wherein Z' represents any divalent group of the formulas (Z-1) to (Z-5) or (Z-7), and X$^1$ and X$^2$ are the same or different and represent independently a chlorine atom, a bromine atom, or an iodine atom), a compound of the following formula (6) (hereinafter, abbreviated to as compound (6)):

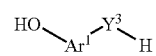

(6)

wherein Ar$^1$ is as defined above, and Y$^3$ represents —O—, —S—, or —Si(R$^{23}$)(R$^{24}$)—, and a compound of the following formula (6) (hereinafter, abbreviated to as compound (6)):

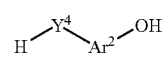

(7)

wherein Ar$^2$ is as defined above, and Y$^4$ represents —O—, —S—, or —Si(R$^{23}$)(R$^{24}$)—, in the presence of a base.

Examples of the compound (5) include 2,4-dichloropyridine, 2,4-dibromopyridine, 2,5-dichloropyridine, 2,5-dibromopyridine, 3,5-dichloropyridine, 3,5-diboromopyridine, 2,3-dichloropyridine, 2,3-diborompyridine, 2,6-dichloropyridine, 2,6-diboromopyridine, 4-methyl-2,6-dichloropyridine, 4-methyl-2,6-diboromopyridine, 2-methyl-4,6-dichloropyridine, 2-methyl-4,6-dibromopyridine, 3,6-dichloropyridazine, 3,6-dibromopyridazine, 4,5-dichloropyridazine, 4,5-dibromopyridazine, 4-methyl-3,6-dichloropyridazine, 4-methyl-3,6-dibromopyridazine, 2,4-dichloropyrimidine, 2,4-diboromopyrimidine, 4,6-dichloropyrimidine, 4,6-diboromopyrimidine, 6-methyl-2,4-dichloropyrimidine, 6-methyl-2,4-diboromopyrimidine, 5-methyl-2,4-dichloropyrimidine, 5-methyl-2,4-diboromopyrimidine, 2,3-dichloropyrazine, 2,3-dibromopyrazine, 2,6-dichloropyrazine, 2,6-dibromopyrazine, 2,6-dichlorotriazine, 2,6-dibromotriazine, 4-(4-morpholino)-2,6-dichlorotriazine, 4-(4-morpholino)-2,6-dibromotriazine, 4-[(1,1,3,3-tetramethylbutyl)amino]-2,6-dichlorotriazine, 4-[(1,1,3,3-tetramethylbutyl)amino]-2,6-dibromotriazine, 1,3-bis(chloromethyl)benzene, 1,3-bis(bromomethyl)benzene, 1,4-bis(chloromethyl)benzene, and 1,4-bis(bromomethyl)benzene.

The compound (6) and the compound (7) may be the same or different, and examples thereof include 4,4'-biphenol, hydroquinone, and 2,6-dihydroxynaphthalene.

The reaction is carried out generally by mixing and bringing the compound (5), the compound (6), the compound (7), and a base into contact with one another in a solvent. In the case where the compound (6) and the compound (7) are the same, an order of mixing is not particularly limited and, in the case where the compound (6) and the compound (7) are different, it is preferable to react either one of the compound (6) and the compound (7) with the compound (5) in the presence of a base and then reacting the other in the presence of a base in order to obtain the alcohol compound (2) in a good yield.

In the case where the compound (6) and the compound (7) are the same, an amount of the compound (6) that may be used is generally 1 to 20 moles, preferably 1.5 to 50 moles per mol of the compound (5). In the case where the compound (6) and the compound (7) are different, an amount of each of them that may be used is generally 1 to 20 moles, preferably 2 to 15 moles per mol of the compound (5).

Example of the base include alkali metal hydroxides such as sodium hydroxide or potassium hydroxide, alkaline earth metal hydroxides such as magnesium hydroxide or calcium hydroxide, alkali metal carbonates such as sodium carbonate or potassium carbonate, alkali metal bicarbonates such as sodium bicarbonate, and alkali metal alkoxides such as sodium methoxide, sodium ethoxide, potassium methoxide, potassium ethoxide, and potassium tert-butoxide, and alkali metal hydroxides and alkali metal carbonates are preferable, and alkali metal hydroxides are more preferable.

In the case where the compound (6) and the compound (7) are the same, an amount of the base that may be used is generally 1 to 10 moles, preferably 2 to 8 moles per mol of the compound (5). In the case where the compound (6) and the compound (7) are different, amounts of the base that may be used for these compounds are generally 1 to 10 moles, preferably 2 to 8 moles per mol of the compound (5), respectively.

Examples of the solvent include alcohol type solvents such as methanol, ethanol, propyl alcohol, butanol, ethylene glycol, and propylene glycol, ketone type solvents such as methyl ethyl ketone and methyl isobutyl ketone, non-protonic polar solvents such as N,N-dimethylformamide, dimethyl sulfoxide, and N-methylpyrrolidone, and ether type solvents such as tetrahydrofuran, dioxane, methoxymethyl ether, diethoxyethane, and water, and mixtures thereof. Non-protonic polar solvents or mixtures of non-protonic polar solvents and water are preferable. An amount of the solvent that may be used is generally 0.5 to 50 parts by weight, preferably 2 to 30 parts per part by weight of the alcohol compound (5).

In the case where the compound (6) and the compound (7) are the same, a reaction temperature is generally 40 to 150° C., preferably 60 to 150° C. In the case where the compound (6) and the compound (7) are different, a reaction temperature is generally 40 to 150° C., preferably 60 to 150° C. In the case where compound (6) and the compound (7) are different from each other and either one of the compound (6) and the compound (7) is reacted first with the compound (5) in the presence of a base and thereafter the other is reacted in the presence of a base, it is preferable that a reaction temperature in the case of the reaction of the other in the presence of a base is higher than that of the reaction of either one of the compound (6) and the compound (7) with the compound (5).

After completion of the reaction, for example, a hydrophilic solvent is added and insoluble matters, which are byproducts, are removed if necessary, followed by concentration or cooling, to separate the alcohol compound (2). The separated alcohol compound (2) may be further purified by a conventional purification means, for example, by recrystallization.

Among alcohol compounds (2), compounds wherein Z is a divalent group of (Z-1) to (Z-5) or (Z-7), and $Y^1$ and $Y^2$ are a single bond can be prepared, for example, by a Grignard coupling reaction of a compound (5) with a compound of the following formula (8):

(8)

wherein $Ar^1$ is as defined above, and $X^3$ represents a chlorine atom, a bromine atom, or an iodine atom, and a compound of the following formula (9):

(9)

wherein $Ar^2$ is as defined above, and $X^4$ represents a chlorine atom, a bromine atom, or an iodine atom, and the reaction may be carried out according to a similar manner known as Grignard coupling reaction.

Among alcohol compounds (2), compounds wherein Z is a divalent group of (Z-6) and $Y^1$ and $Y^2$ are the same or different and represent independently —O—, —S—, or —Si($R^{23}$)($R^{24}$)— can be prepared, for example, by reacting a compound of the following formula (10):

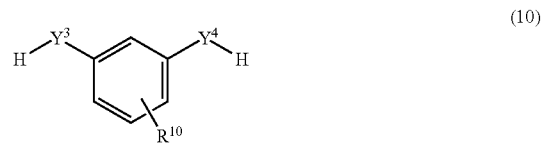

(10)

wherein $R^{10}$, $Y^3$, and $Y^4$ are independently as defined above, the compound of the formula (8), and the compound of formula (9) in the presence of a base. Such a reaction may be carried out in a similar manner as in the above-mentioned reaction of the compound (5), the compound (6), and the compound (7). Among alcohol compounds (2), compounds (2) wherein Z is a divalent group of (Z-6), and $Y^1$ and $Y^2$ are a single bond can be prepared, for example, by carrying out a Grignard coupling reaction using a compound of the following formula (11):

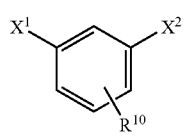

(11)

wherein $R^{10}$, $X^1$ and $X^2$ are as defined above, in place of the compound (5) in a Grignard coupling reaction of the compound (5), the compound of the formula (8) and the compound of the formula (9).

The compound (12) is produced, for example, by a process of reacting a compound of formula (15):

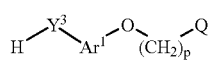

(15)

wherein $Ar^1$, $Y^3$, Q and p are as defined above, with a compound of formula (16):

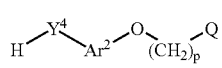

(16)

wherein $Ar^2$, $Y^4$, Q and p are as defined above, and a compound of formula (5) as defined above, in the presence of a base.

The compound of formula (15) is typically obtained by reacting a compound of formula (14):

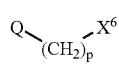

(14)

wherein Q and p are as defined above, and $X^6$ represents a chlorine, bromine, or iodine atom, with a compound of formula (6) as defined above, in the presence of a base.

The compound of formula (16) can be typically obtained by reacting the compound of formula (14) as defined above, with a compound of formula (7) as defined above, in the presence of a base. The compound (16) and the compound (17) may be the same or different.

Examples of the compound (14) include, for example, 2-chloroethanol, 2-bromoethanol, 2-(2-chloroethoxy)ethanol, 2-chlroethylamine and the like. When Q is a hydroxyl group in the compounds (14), (15) and (16), these compound having protected hydroxyl group, protected with a protective group such as benzyl or tetrahydropyranyl group, may be used. The amount of the compound (14) that may be used in the reaction with the compound (6) is typically 1 to 50 moles, preferably 1 to 20 moles per mol of the compound (6). The base described above can be used in this reaction and the amount of the base that may be used is ususallyl to 5 moles per mol of the compound (6).

The reaction of the compound (6) and the compound (14) is conducted usually in a suitable solvent in the presence of a base under normal pressure or reduced pressure typically at a temperature of 10 to 150° C., and the mixing order thereof is not limited. Examples of the solvent that may be suitably used include, for example, those solvents as exemplified above for the solvent suitably used in the reaction of compound (2) and compound (3). In this reaction water may be by produced with the progress of the reaction depending upon the base used and the resulting water may be azeotropically removed from the reaction system. The amount of compound (14) that may be used in the reaction with compound (7) is typically 1 to 50 moles, preferably 1 to 20 moles per mol of the compound (7). As the base that may be used in this reaction, the same base as described above can be used and the amount thereof that may be used is typically 1 to 5 moles per mol of compound (7). The reaction can be carried out in a similar manner as in the reaction of the compound (14) with the compound (6) as described above.

Examples of the compounds (15) and (16) include, for example, 4-[4-(2-hydrocyethoxy)phenyl]phenol, 4-[4-(2-aminoethoxy)phenyl]phenol, 4-[4-(5-hydroxy-3-oxapentyloxy)phenyl]phenol, 4-(4-(8-hydroxy-3,6-dioxaoctyloxy]phenyl]phenol and the like.

The reaction of compounds (15), (16) and (5) can be carried out in a similar manner as in the reaction of compounds (5), (6) and (7).

Then, the epoxy composition of the present invention will be explained. The epoxy resin of the present invention is an epoxy composition containing an epoxy compound (1) and a curing agent, and is obtained by mixing the epoxy compound with the curing agent either as they are or in a solvent. The composition may contain one kind epoxy compound (1) and the curing agent or two or more different types of epoxy compounds (1) and the curing agent. Examples of the solvent include ketone type solvents such as methyl ethyl ketone and methyl isobutyl ketone, non-protonic polar solvents such as dimethyl sulfoxide and N-methylpyrrolidone, ester type solvents such as butyl acetate, and glycol type solvents such as propylene glycol monomethyl ether.

As the curing agent, a curing agent having in its molecule at least two functional groups capable of curing-reacting with an epoxy group can be used, and examples thereof include a curing agent having amino groups as the functional group, which is referred to as an amino type curing agent, a curing agent having hydroxyl groups as the functional group, which is referred to as a phenol type curing agent, and a curing agent having carboxyl groups as the functional group, which is referred to as an acid anhydride type curing agent. Preferred are the amine type curing agent and the phenol type curing agent. Inter alia, the amine type curing agent is preferable.

Examples of the amine type curing agents include $C_{2-20}$ aliphatic polyamines such as ethylenediamine, trimethylenediamine, tetramethylenediamine, or hexamethylenediamine, aromatic polyamines such as p-xylenediamine, m-xylenediamine, 1,5-diaminonaphthalene, m-phenylenediamine, p-phenylenediamine, 4,4'-diamnodiphenylmethane, 4,4'-diaminodiphenylethane, 4,4'-diaminodiphenylpropane, 4,4'-diaminodiphenyl ether, 1,1-bis(4-aminophenyl)cyclohexane, 4,4'-diaminodiphneylsulfone, or bis(4-aminophenyl)

phenylmethane, and alicyclic polyamines such as 4,4'-diaminodicyclohexane or 1,3-bisaminomethylcyclohexane and dicyanodiamide, and aromatic polyamines are preferable and, among them, 4,4'-diaminodiphenylmethane, 4,4'-diaminodiphenylethane, 1,5diaminonaphthalene and p-phenylenediamine are more preferable.

Examples of the phenol type curing agents include, for example, phenol resins, phenolaralkyl resins (having phenylene skeleton, diphenylene skeleton etc.), naphtholaralkyl resins, and polyoxystyrene resins.

Examples of the phenol resins include, for example, resol-type phenol resins such as aniline-modified resol resin or dimethyl ether resol resin, novolak-type phenol resins such as phenol novolak resin, cresol novolak resin, tert-butylphenol novolak resin or nonylphenol novolak resin, special phenol resins such as dicyclopentadiene-modified phenol resin, terpene-modified phenol resin, or triphenol-methane-type resin, and examples of the polyoxystyrene resins include, for example, poly(p-oxystyrene).

Examples of acid anhydrides include maleic anhydride, phthalic anhydride, pyromellitic anhydride and trimellitic anhydride.

Such curing agents are used in such an amount that a total amount of functional groups, in the curing agents, capable of curing-reacting with the epoxy groups is generally 0.5 to 1.5 moles, preferably 0.9 to 1.1 moles per mol of the total amount of the epoxy groups in the epoxy compound (1).

The epoxy composition of the present invention may contain the above-mentioned solvent as described above in addition to the epoxy compound (1) and the curing agent and also other epoxy compounds and a variety of additives as far as these compounds do not have any adverse effects on the desired performance of the cured epoxy resin product obtained by curing the epoxy composition. Examples of other epoxy compounds include bisphenol A-type epoxy compounds, o-cresol-type epoxy compounds, and epoxy compounds such as biphenol diglycidyl ether, 4,4'-bis(3,4-epoxybuten-1-yloxy)phenyl benzoate, naphthalene diglycidyl ether, and α-methylstilbene-4,4'-diglycidyl ether. Examples of the additives include silica powders such as fused and pulverized silica powder, fused spherical silica powder, crystalline silica powder, and secondarily agglomerated silica powder, fillers such as alumina, titanium white, aluminum hydroxide, talc, clay, mica, and glass fiber, curing promoting agents such as triphenylphosphine, 1,8-azabicyclo[5.4.0]-7-undecene and 2-methylimidazole; coupling agents such as γ-glycidoxypropyltrimethoxysilane, coloring agents such as carbon black, low stress components such as silicone oil and silicone rubber; release agents such as natural waxes, synthetic waxes, higher fatty acids and their metal salts, and paraffins, and antioxidants. Contents of other epoxy resins and such additives are not particularly limited as far as the contents are such that desired performance of the cured epoxy resin product obtained by curing the epoxy composition of the invention is not deteriorated.

Then, the cured epoxy resin product of the present invention will be explained. The cured epoxy resin product of the present invention can be prepared by curing the epoxy composition containing the above-mentioned epoxy compound (1) and a curing agent.

The cured epoxy resin product of the present invention may be a cured epoxy resin product obtained by curing one kind epoxy compound (1) and the curing agent, or a cured epoxy resin product obtained by curing two or more different types of epoxy compounds (1) and the curing agent.

A method for curing the epoxy composition may be, for example, a curing method by heating the epoxy composition as it is, a method by heating and melting the epoxy composition, pouring the melt into a mold, and further heating the mold, a method by melting the epoxy composition and injecting and curing the resulting melt to a previously heated mold by a transfer molding machine, a method by partially curing the epoxy composition (so-called B-stage), filling a mold with a powder obtained by pulverizing the partially cured product, and melting-molding the packed powder, and a method by dissolving the epoxy composition in a solvent if necessary, bringing the solution into B-stage while stirring, casting the obtained solution, and removing the solvent by drying with air blow, followed by heating for a prescribed time while applying a pressure with a press if necessary.

Finally, a prepreg obtained by impregnating or coating a substrate with the epoxy composition of the present invention and semi-curing the composition will be described. The prepreg can be prepared by diluting the epoxy composition of the present invention with a solvent if necessary, impregnating or coating a substrate with the obtained solution, heating the impregnated or coated substrate to semi-cure the epoxy compound in the substrate or on it. Examples of the substrate include woven fabrics or non-woven fabrics made of inorganic fibers such as glass fiber woven fabric and woven fabrics or non-woven fabrics made of organic fibers such as polyester can be exemplified. By using such a prepreg, laminated sheets can be easily prepared by a common method.

EXAMPLES

The present invention will be described in more detail with reference to Examples, however the present invention is not limited to these Examples. Analysis in preparation of epoxy compounds was carried out by high performance liquid chromatography (hereinafter, abbreviated as LC)

Example 1

Preparation Example of Epoxy Compound No. 1

73.3 g of 4,4'-biphenol, 366.7 g of dimethyl sulfoxide, and 67.7 g of a 48% by weight aqueous sodium hydroxide solution were charged into a 1 L four-neck flask equipped with a thermometer, a condenser tube and a stirrer, and the mixture was heated to an inner temperature of about 80° C. to dissolve it. Thereafter, a solution obtained by dissolving 29.1 g of 2,6-dichloropyridine in 183.3 g of dimethyl sulfoxide was added dropwise over 2 hours, an inner temperature was raised to 130° C., and the mixture was reacted by stirring at the same temperature for 7 hours. After completion of the reaction, the insoluble matters were removed by filtration at an inner temperature of about 100° C., and 158.6 g of water was charged into the resulting filtrate and cooled to a room temperature to precipitate a crystal. The precipitated crystal was filtered and washed with 350 g of water and dried at an inner temperature 80° C. for 12 hours under reduced pressure to obtain 73.3 g of a crystal of 2,6-bis[4-(4-hydroxyphenyl)phenoxy]pyridine. Apparent yield: 83.3%. Mass spectrometric value (FD-MS): m/z=447, melting point: 200° C. or higher 20 g of the above-obtained crystal of 2,6-bis[4-(4-hydroxyphenyl)phenoxy]pyridine, 80 g of epichlorohydrin, 10 g of dimethyl sulfoxide, and 4.4 g of sodium hydroxide were charged into a 1 L four-neck flask equipped with a thermometer, a condenser tube and a stirrer, an inner pressure was reduced to about 6 kPa, and the mixture was reacted for 4 hours while refluxing at an inner temperature of about 50°

C. An inner temperature was raised to about 70° C., followed by further reaction for 1 hour while refluxing.

The reaction was carried out while water produced as a byproduct was distilled and removed out of the system. After completion of the reaction, the reaction mixture was concentrated at an inner pressure of about 6 kPa and an inner temperature of about 70° C. to remove the remaining epichlorohydrin. After insoluble matters in the concentrated residue were removed by filtration, the filtrate was cooled to a room temperature to precipitate a crystal. After the precipitated crystal was collected by filtration and washed with a mixed solution of 30 g of dimethyl sulfoxide and 100 g of methanol, the crystal was dried at an inner temperature of 80° C. for 12 hours under reduced pressure to obtain 14.8 g of a crystal of 2,6-bis[4-4-(oxiranylmethoxy)phenyl]phenoxy]pyridine. Purity: 96.6% (LC area percentage value), apparent yield; 59.2%. Mass spectrometric value (FD-MS): m/z=559, melting point: 157 to 160° C.

Example 2

Preparation Example of Epoxy Compound No. 2

67.8 g of 4,4'-biphenol, 314.6 g of dimethyl sulfoxide, 58.1 g a 48% by weight aqueous sodium hydroxide solution, and 29.1 g of water were charged into a 1 L four-neck flask equipped with a thermometer, a condenser tube and a stirrer, and the mixture was heated to an inner temperature of about 80° C. to dissolve it. Thereafter, a solution obtained by dissolving 20.1 g of 3,6-dichloropyridazine in 41.4 g of dimethyl sulfoxide was added dropwise over 1 hour, and an inner temperature was raised to 100° C., followed by stirring at the same temperature for 7 hours to react the mixture. After completion of the reaction, the insoluble matters were removed by filtration at an inner temperature of about 100° C. The insoluble matters were washed twice with 30 g of dimethyl sulfoxide and the resulting washing solution was combined with the previously obtained filtrate. 7.6.7 g of 20% by weight hydrochloric acid was charged into the combined filtrate, and cooled to a room temperature to precipitate a crystal. The precipitated crystal was collected by filtration and washed with 200 g of water, and dried at an inner temperature of 80° C. for 12 hours under reduced pressure to obtain 42.6 g of a crystal of 2,6-bis[4-(4-hydroxyphenyl)phenoxy]pyridazine. Apparent yield: 70.0%. Mass spectrometric value (FD-MS): m/z=448, melting point: 200° C. or higher 42 g of the above-obtained crystal of 2,6-bis[4-(4-hydroxyphenyl)phenoxy]pyridazine, 168 g of epichlorohydrin, 84 g of dimethyl sulfoxide, and 7.7 g of sodium hydroxide were charged into a 1 L four-neck flask equipped with a thermometer, a condenser tube and a stirrer, an inner pressure was reduced to about 6 kPa, and the mixture was reacted for 4 hours while refluxing at an inner temperature of about 50° C. An inner temperature was raised to about 70° C., followed by further reaction for 1 hour while refluxing. The reaction was carried out while water produced as a byproduct was distilled and removed out of the system. After completion of the reaction, the resulting reaction mixture was concentrated at an inner pressure of about 6 kPa and an inner temperature of about 70° C. to remove the remaining epichlorohydrin. 126 g of dimethyl sulfoxide was charged into the concentrated residue, and cooled to a room temperature to precipitate a crystal. The precipitated crystal was collected by filtration and the resulting crystal was mixed with 354.5 g of dimethyl sulfoxide and heated to an inner temperature of 80° C. The insoluble matters were removed by filtration at the same temperature, and the filtrate was cooled to a room temperature to obtain 7.1 g of a crystal of 2,6-bis[4-[4-(oxiranylmethoxy)phenyl)phenoxy]pyridazine. Purity: 94.5% (LC area percentage value), apparent yield; 13.5%. Mass spectrometric value (FD-MS): m/z=560, melting point: 160° C.

Example 3

Preparation Example of Epoxy Compound No. 3

57.2 g of 4,4'-biphenol, 289.6 g of dimethyl sulfoxide, 52.7 g of a 48% by weight aqueous sodium hydroxide solution, and 30 g of water were charged into a 1 L four-neck flask equipped with a thermometer, a condenser tube and a stirrer, and the mixture was heated to an inner temperature of about 80° C. to dissolve it. Thereafter, a solution obtained by dissolving 20 g of 2,4-dichloro-6-methylpyrimidine in 60.2 g of dimethyl sulfoxide was added dropwise over 1 hour, and an inner temperature was raised to 120° C., followed by reaction at the same temperature for 7 hours while stirring. After completion of the reaction, the insoluble matters were removed by filtration at an inner temperature of about 100° C. 68.4 g of 20% by weight hydrochloric acid was charged with the resulting filtrate, and cooled to a room temperature to precipitate a crystal. The precipitated crystal was collected by filtration, washed with 200 g of water, and dried at an inner temperature of 80° C. for 12 hours under reduced pressure to obtain 31.5 g of a crystal of 2,4-bis[4-(4-hydroxyphenyl)phenoxy]-6-methylpyrimidine. Apparent yield: 55.5%. Mass spectrometric value (FD-MS): m/z=462, melting point: 200° C. or higher 36.5 g of a crystal of 2,4-bis[4-(4-hydroxyphenyl)phenoxy]-6-methylpyrimidine obtained in the above-mentioned manner, 146.2 g of epichlorohydrin, 73.1 g of dimethyl sulfoxide, and 6.6 g of sodium hydroxide were charged into a 1 L four-neck flask equipped with a thermometer, a condenser tube and a stirrer, an inner pressure was reduced to about 6 kPa, and the mixture was reacted for 4 hours while refluxing at an inner temperature of about 50° C. An inner temperature was raised to about 70° C., and the mixture was further reacted for 1 hour while refluxing. The reaction was carried out while water produced as a byproduct was distilled and removed out of the system. After completion of the reaction, the reaction mixture was concentrated at an inner pressure of about 6 kPa and an inner temperature of about 70° C. to remove the remaining epichlorohydrin. 109.5 g of dimethyl sulfoxide was charged into the concentrated residue, and the insoluble matters were removed by filtration at an inner temperature of 55° C. The insoluble matters were washed twice with 73 g of dimethyl sulfoxide and the resulting washing solution was combined with the previously obtained filtrate. 200 g of methanol was charged into the combined filtrate, and a crystal was allowed to precipitate. The precipitated crystal was washed twice with 100 g of methanol and then dried at an inner temperature of 80° C. for 12 hours under reduced pressure to obtain 13.2 g of a crystal of 2,4-bis[4-[4-(oxiranylmethoxy)phenyl)phenoxy]-6-methylpyrimidine. Purity: 87.0% (LC area percentage value), apparent yield: 29.1%. Mass spectrometric value (FD-MS): m/z=574, melting point: 180° C.

Example 4

Preparation Example of Epoxy Compound No. 4

80 g of 4,4'-biphenol, 400 g of dimethyl sulfoxide, and 90.0 g of a 39% by weight aqueous sodium hydroxide solution, and 15 g of water were charged into a 1 L four-neck flask equipped with a thermometer, a condenser tube and a stirrer, and the mixture was heated to an inner temperature of about 80° C. to dissolve it. Thereafter, a solution obtained by dissolving 25.4 g of 2,6-dichloropyridine in 70.7 g of dimethyl sulfoxide was added dropwise over 4.5 hours, and an inner temperature was raised to 80° C., followed by reaction at the same temperature for 1 hour while stirring. After completion of the reaction, 400 mL of dimethyl sulfoxide was charged therein at an inner temperature of about 80° C., cooled to a room temperature and the insoluble matters were removed by filtration. The insoluble matters were washed with 200 mL of dimethyl sulfoxide, and the washing solution was combined with the previously obtained filtrate. After combining, 190 mL of 10% by weight hydrochloric acid and 1,400 mL of water added to the filtrate to precipitate a crystal. The precipitated crystal was collected by filtration, washed with 400 mL of water three times and dried at an inner temperature of 70° C. for 3 hours and further at an inner temperature of 80° C. for 5 hours under reduced pressure to obtain 39.1 g of a white solid of 2-[4-(4-hydroxyphenyl)phenoxy]-6-chlorolpyridine. Apparent yield: 76.5%.

37 g of hydroquinone, 100 g of dimethyl sulfoxide, and 17.8 g of a 39% by weight aqueous sodium hydroxide solution were charged into a 1 L four-neck flask equipped with a thermometer, a condenser tube and a stirrer, and the mixture was heated to an inner temperature of 130° C. to dissolve it. Thereafter, a solution obtained by dissolving 10 g of the above-obtained white solid of 2-[4-(4-hydroxyphenyl)phenoxy]-6-chloropyridine in 40 g of dimethyl sulfoxide was added dropwise over 1 hour, followed by reaction at an inner temperature of about 130° C. for 6 hours while stirring. After completion of the reaction, the resulting reaction solution was cooled to a room temperature, 1,240 g of water was added, and the precipitated crystal was collected by filtration, washed with 100 mL of water three times and then dried at an inner temperature about of 80° C. for 5 hours under reduced pressure condition to obtain 11.3 g of a white solid of 2-[4-(4-hydroxyphenyl)phenoxy]-6-(4-hydroxyphenoxy)pyridine. Apparent yield: 90.7%. Mass spectrometric value (FD-MS): m/z=371, melting point: 200° C. or higher.

15.1 g of a white solid of 2-[4-(4-hydroxyphenyl)phenoxy]-6-(4-hydroxyphenoxy)pyridine obtained in the above-mentioned manner, 60 g of epichlorohydrin, 29.6 g of dimethyl sulfoxide, and 3.3 g of sodium hydroxide were charged, and an inner pressure was reduced to about 6 kPa, followed by reaction for 4 hours while refluxing at an inner temperature of about 50° C. An inner temperature was raised to about 70° C., followed by further reaction for 1 hour while refluxing at the same temperature. The reaction was carried out while water produced as a byproduct was distilled and removed out of the system. After completion of the reaction, the resulting reaction solution was concentrated at an inner pressure of about 6 kPa and an inner temperature of about 70° C. to remove the remaining epichlorohydrin. 22.5 g of dimethyl sulfoxide was charged into the concentrated residue, and the insoluble matters were removed by filtration. The filtrate was concentrated to obtain 22.5 g of a crude crystal. 20 g of the crude crystal and 30 g of tetrahydrofuran were mixed, and heated to an inner temperature of 55° C. to dissolve the crystal. After 10 g of ethyl acetate and 60 g of n-hexane were charged therein, the mixture was cooled to a room temperature to precipitate a crystal. The precipitated crystal was collected by filtration, washed twice with 70 g of a mixed solution of ethyl acetate and n-hexane and then dried at an inner temperature of 80° C. for 12 hours under reduced pressure to obtain 14.8 g of a crystal of 2-[4-[4-(oxiranylmethoxy)phenyl]phenoxy]-6-[4-(oxiranylmethoxy)phenoxy]pyridine. Purity: 91.3% (LC area percentage value), apparent yield: 62.5%. Mass spectrometric value (FD-MS): m/z=483, melting point: 110 to 114° C.

Example 5

Preparation Example of Epoxy Composition and Cured Epoxy Resin Product No. 1

28 Parts by weight of 2,6-bis[4-[4-(oxiranylmethoxy)phenyl]phenoxy]pyridine obtained in Example 1 and 5 parts by weight of 4,4'-diaminodiphenylmethane were mixed to obtain an epoxy composition. The resulting epoxy composition was heated from room temperature to 180° C. by a hot stage (FP 82 HT and FP 90, manufactured Mettler-Toledo K.K.) to obtain a cured epoxy resin product. A Schilieren pattern was observed at about 150 to 160° C. by observation with a polarizing light microscope (XTP-11 manufactured by Nikon) and the resulting product was found to be a cured epoxy resin product having liquid crystal properties.

Example 6

Preparation Example of Epoxy Composition and Cured Epoxy Resin Product No. 2

50 Parts by weight of 2,6-bis[4-[4-(oxiranylmethoxy)phenyl]phenoxy]pyridine obtained in Example 1 and 9 parts by weight of 4,4'-diaminodiphenylmethane were mixed to obtain an epoxy composition. The resulting epoxy composition was melted, placed into a hollow part of a plate-like mold heated at about 160° C. and allowed to stand at about 100 to 180° C. for about 10 hours to obtain a plate-like cured epoxy resin product.

The resulting cured epoxy resin product was cut into a disk having a diameter of 1 cm and a thickness of 1 mm, and a thermal conductivity in a thickness direction and in an in-plane direction. A thermal conductivity was calculated from a product of a heat diffusion ratio in a thickness direction or an in-plane direction measured by a laser flash method, and a specific heat capacity, and a density of the sample and the measurement was carried out at room temperature. A thermal conductivity in a thickness direction was as high as 0.58 W/m·K, a thermal conductivity in an in-plane direction was as high as 0.54 W/m·K, and it was found that the resulting cured epoxy resin product is a cured epoxy resin product having an excellent heat conductivity.

Example 7

Preparation Example of Epoxy Composition and Cured Epoxy Resin Product No. 3

50 Parts by weight of 2,6-bis[4-[4-(oxiranylmethoxy)phenyl]phenoxy]pyridine obtained in Example 1, 9 parts by weight of 4,4'-diaminodiphenylmethane, and alumina as a filler (having average particle diameter of 2 μm manufactured by Showa Denko K.K.) were mixed to obtain an epoxy composition. The resulting epoxy composition was melted, placed into a hollow part of a plate-like mold heated at about 160° C. and allowed to stand at about 100 to 180° C. for about 10 hours to obtain a plate-like cured epoxy resin product.

The resulting cured epoxy resin product was cut into a disk having a diameter of 1 cm and a thickness of 1 mm, thermal conductivities in a thickness direction and in an in-plane direction were measured by a laser flash method, and it was found that a thermal conductivity in a thickness direction was as high as 1.8 W/m·K and a thermal conductivity in an in-plane direction was as high as 1.7 W/m·K and that the resulting cured epoxy resin product is a cured epoxy resin product having an excellent thermal conductivity.

Example 8

Preparation Example of Epoxy Composition and Cured Epoxy Resin Product No. 4

100 Parts by weight of 2,6-bis[4-[4-(oxiranylmethoxy)phenyl]phenoxy]pyridine obtained in Example 1, 22 parts by weight of 1,5-diaminonaphthalene as a curing agent (manufactured by Wako Pure Chemical Industries, Ltd.), and 285 parts by weight of methyl isobutyl ketone as a solvent were added, and a resin solid matter in this resulting resin composition was adjusted to be 30% by weight, followed by stirring.

A glass fiber fabric having a thickness of 0.2 mm was impregnated with the resulting epoxy composition and dried by heating to obtain a prepreg. Four of such prepregs were stacked and integrated by thermal press molding at a temperature of about 175° C. and a pressure of 4 MPa for 90 minutes to obtain a laminated sheet having a thickness of 0.8 mm. A plate-like sample of 60 mm×120 mm was cut out of the laminated sheet and subjected to thermal conductivity measurement. The thermal conductivity measurement was carried out at a room temperature according to a probe method. As a result, a thermal conductivity as high as 0.89 W/m·K was obtained.

Comparative Example 1

28 Parts by weight of bisphenol A-type epoxy compound (EP-828 manufactured by Japan Epoxy Resin) and 8 parts by weight of 4,4'-diaminodiphenylmethane were mixed and the mixture was heated from a room temperature to 180° C. by a hot stage (FP 82 HT and FP 90, manufactured Mettler-Toledo) to obtain a general-use cured epoxy resin product. No polarization extinction was observed at a temperature of from room temperature to 180° C. by observation by using a polarizing light microscope (XTP-11 manufactured by Nikon), and it was found that the resulting cured epoxy resin product had no liquid crystal property.

Comparative Example 2

50 Parts by weight of bisphenol A-type epoxy compound and 15 parts by weight of 4,4'-diaminodiphenylmethane were mixed, a melt of the mixture was placed into a hollow part of a plate-like mold heated at about 100° C. and allowed to stand at about 100 to 180° C. for about 10 hours to obtain a plate-like cured epoxy resin product.

The resulting cured epoxy resin product was cut into a disk having a diameter of 1 cm and a thickness of 1 mm, a thermal conductivity in a thickness direction and in an in-plane direction was measured by a laser flash method, and it was found that a thermal conductivity in a thickness direction was as low as 0.21 W/m·K and a thermal conductivity in an in-plane direction was as low as 0.18 W/m·K.

Comparative Example 3

100 Parts by weight of bisphenol A-type epoxy compound, 40 parts by weight of 1,5-diaminonaphthalene as a curing agent (manufactured by Wako Pure Chemical Industries, Ltd.), and 327 parts by weight of methyl isobutyl ketone as a solvent were added, and a resin solid matter in this resin composition was adjusted to 30% by weight, followed by stirring.

A glass fiber fabric having a thickness of 0.2 mm was impregnated with the resulting epoxy composition and dried by heating to obtain a prepreg. Four of such prepregs were stacked and integrated by thermal press molding at a temperature of about 175° C. and a pressure 4 MPa for 90 minutes to obtain a laminated sheet having a thickness of 0.8 mm. A plate-like sample of 60 mm×120 mm was cut out of the laminated sheet and subjected to thermal conductivity measurement. The thermal conductivity measurement was carried out at a room temperature according to a probe method. As a result, it was found that a thermal conductivity was 0.45 W/m·K.

Example 9

Preparation Example of Epoxy Composition and Cured Epoxy Resin Production No. 5

According to the same manner as that of Example 5 except that 2,6-bis[4-[4-(oxiranylmethoxy)phenyl]phenoxy]pyridazine obtained in Example 2 was used in place of 2,6-bis[4-[4-(oxiranylmethoxy)phenyl]phenoxy]pyridine obtained in Example 1, an epoxy resin composition and a cured epoxy resin product having liquid crystal properties were obtained.

Example 10

Preparation Example of Epoxy Composition and Cured Epoxy Resin Product No. 6

According to the same manner as that of Example 5 except that 2,4-bis[4-(4-(oxiranylmethoxy)phenyl]phenoxy]-6-methylpyrimidine obtained in Example 3 was used in place of 2,6-bis[4-[4-(oxiranylmethoxy)phenyl]phenoxy]pyridine obtained in Example 1, an epoxy resin composition and a cured epoxy resin product having liquid crystal properties were obtained.

Example 11

Preparation Example of Epoxy Composition and Cured Epoxy Resin Product No. 7

According to the same manner as that of Example 6 except that 2-[4-[4-(oxiranylmethoxy)phenyl]phenoxy]-6-[4-(oxiranylmethoxy)phenoxy]pyridine obtained in Example 4 was used in place of 2,6-bis[4-[4-(oxiranylmethoxy)phenyl]phenoxy]pyridine obtained in Example 1, a cured epoxy resin product having a thermal conductivity in an in-plane direction of 0.24 W/m·K was obtained.

Example 12

Preparation Example of Epoxy Compound No. 5

100 g of 4,4'-biphenol, 500 g of dimethyl sulfoxide, and 89.5 g of a 48% by weight aqueous sodium hydroxide solution and 50 g of water were charged into a 1 L four-neck flask equipped with a thermometer, a condenser tube and a stirrer, and the mixture was heated to an inner temperature of about 80° C. to dissolve it. Thereafter, a solution obtained by dissolving 37.6 g of 1,3-bis(chloromethyl)benzene in 112.8 g of dimethyl sulfoxide was added dropwise over 1 hour, and an inner temperature was raised to 120° C., followed by reaction at the same temperature for 1 hour while stirring. After completion of the reaction, the resulting reaction solution was poured into 1,500 g of water, the resulting crystal was filtered, washed with 300 g of water twice and dried at an inner temperature of 80° C. for 12 hours to obtain 97.9 g of a crystal of 1,3-bis[4-(4-hydroxyphenyl)phenoxymethyl]benzene. Apparent yield: 96.0%. Mass spectrometric value (FD-MS): m/z=474, melting point: 200° C. or higher 10 g of the above-obtained crystal of 1,3-bis[4-(4-hydroxyphenyl)phenoxymethyl]benzene, 61 g of epichlorohydrin, 130 g of dimethyl sulfoxide, and 1.8 g of sodium hydroxide were charged into a 1 L four-neck flask equipped with a thermometer, a condenser tube and a stirrer, and an inner pressure was reduced to about 6 kPa, followed by reaction at an inner temperature about 50° C. while refluxing for 4 hours. An inner temperature was raised to about 70° C., followed by further reaction at the same temperature for 1 hour while refluxing. After completion of the reaction, the resulting reaction solution was poured into 650 g of water, and the precipitated crystal was collected by filtration, washed with 100 g of water twice and recrystallized by using 97 g of tetrahydrofuran to obtain 2.0 g of 1,3-bis[4-(4-oxiranylmethoxy)-phenyl]phenoxymethyl)benzene. Purity: 92.3% (LC area percentage value), Apparent yield: 16.2%. Mass spectrometric value (FD-MS): m/z=586, melting point: 225° C.

INDUSTRIAL APPLICABILITY OF THE INVENTION

The novel epoxy compound of the present invention is useful for producing a cured epoxy resin product having liquid crystal properties by curing with a curing agent. The cured epoxy resin product of the present invention exhibits good heat conductivity and is useful as an insulating material requiring high heat releasability such as a printed circuit substrate and the like.

The invention claimed is:

1. An epoxy compound of formula (1):

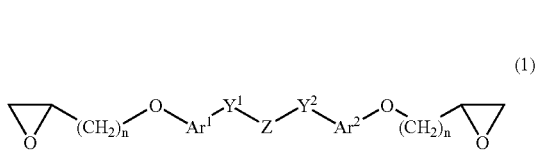

(1)

wherein n represents an integer of 1 to 4,
the —$(CH_2)_n$— group may have inserted —O— between the methylene groups,
Z represents any one of divalent groups of the following general formulas (Z-1) to (Z-3):

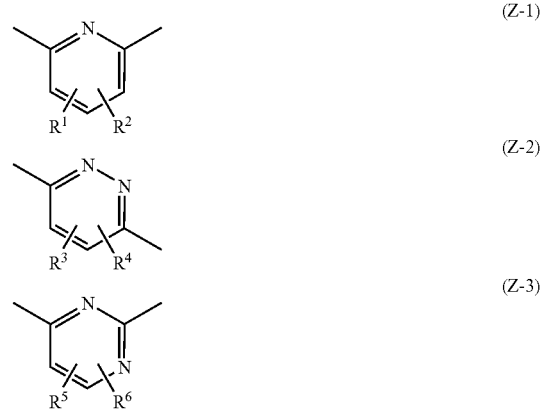

wherein $R^1$, $R^{b\,2}$, $R^3$, $R^4$, $R^5$ and $R^6$ are the same or different and represent independently a hydrogen atom or a $C_{1-1}$ alkyl group,
$Ar^1$ is a group of the following formula (A-1), and $Ar^2$ is a group of the following formula (A-1) or (A-3):

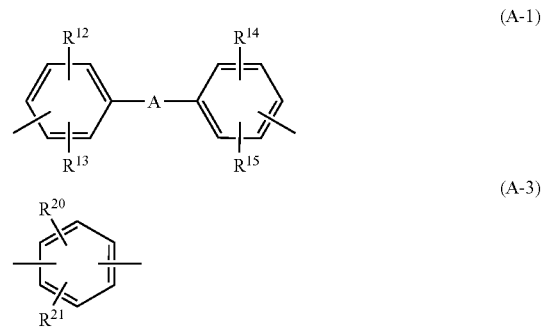

wherein A represents a single bond and
wherein $R^{12}$, $R^{13}$, $R^{14}$, $R^{15}$, $R^{20}$ and $R^{21}$ are the same or different and represent independently a hydrogen atom, a halogen atom, $C_{1-4}$ alkyl group, a $C_{1-8}$ alkoxy group, a cyano group, or a nitro group,
$Y^1$ and $Y^2$, —O—.

2. The epoxy compound according to claim 1, wherein $Ar^1$ and $Ar^2$ in formula (1) are the same or different and represent independently a group of the following formula:

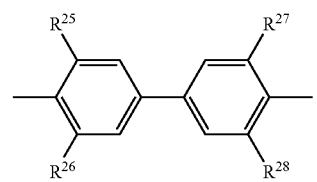

wherein $R^{25}$, $R^{26}$, $R^{27}$ and $R^{28}$ are the seine or different and represent independently a hydrogen atom or a methyl group.

3. The epoxy compound according to claim 1, wherein $Ar^1$ and $Ar^2$ in formula (1) represent the same group of the following formula:

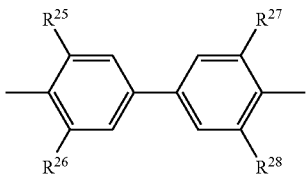

wherein $R^{25}$, $R^{26}$, $R^{27}$ and $R^{28}$ are the seine or different and represent independently a hydrogen atom or a methyl group.

4. An epoxy composition, which comprises the epoxy compound as defined in claim 1 and a curing agent.

5. The epoxy composition according to claim 4, wherein the curing agent is an amine-type curing agent or a phenol type curing agent.

6. A cured epoxy resin product obtained by curing the epoxy composition as defined in claim 4.

7. A prepreg obtained by impregnating or coating a substrate with the epoxy composition of claim 4 and then semi-curing the epoxy composition.

8. An epoxy composition, which comprises the epoxy compound as defined in claim 2 and a curing agent.

9. An epoxy composition, which comprises the epoxy compound as defined in claim 3 and a curing agent.

10. A cured epoxy resin product obtained by curing the epoxy composition as defined in claim 5.

11. A prepreg obtained by impregnating or coating a substrate with the epoxy composition of claim 5 and then semi-curing the epoxy composition.

* * * * *